United States Patent [19]

Leif et al.

[11] Patent Number: 5,188,935
[45] Date of Patent: * Feb. 23, 1993

[54] REAGENT SYSTEM AND METHOD FOR IDENTIFICATION, ENUMERATION AND EXAMINATION OF CLASSES AND SUBCLASSES OF BLOOD LEUKOCYTES

[75] Inventors: Robert C. Leif, Coral Gables; Stephen L. Ledis, Hialeah; Robert I. Feinberg, Sunrise, all of Fla.

[73] Assignee: Coulter Electronics, Inc., Hialeah, Fla.

[*] Notice: The portion of the term of this patent subsequent to Jun. 14, 2005 has been disclaimed.

[21] Appl. No.: 611,381

[22] Filed: Nov. 13, 1990

Related U.S. Application Data

[63] Continuation of Ser. No. 866,985, May 15, 1986, abandoned, which is a continuation of Ser. No. 615,961, May 31, 1984, abandoned.

[51] Int. Cl.$^5$ .......................................... G01N 33/569
[52] U.S. Cl. .............................. 435/7.24; 250/461.2; 435/29; 435/34; 435/39; 436/17; 436/63; 436/519; 436/536; 436/546
[58] Field of Search ..................... 250/461.2; 356/39; 424/3, 7.1; 436/63, 10, 17, 519; 435/536, 546, 2, 29, 30, 34, 39, 7.24

[56] References Cited

U.S. PATENT DOCUMENTS

| | | | |
|---|---|---|---|
| 3,446,751 | 5/1969 | Weichselbaum | 424/3 X |
| 3,710,933 | 1/1973 | Fulwyler et al. | 356/39 X |
| 3,883,247 | 5/1975 | Adams | 356/39 |
| 3,884,579 | 5/1975 | Mauthner | 436/17 |
| 3,916,205 | 10/1975 | Kleinerman | 356/39 X |
| 4,284,412 | 8/1981 | Hansen et al. | 23/230 B |
| 4,286,963 | 9/1981 | Ledis et al. | 436/63 |
| 4,420,558 | 12/1983 | De Mey et al. | 436/63 X |
| 4,492,752 | 1/1985 | Hoffman et al. | 436/63 X |
| 4,493,821 | 1/1985 | Harrison | 436/17 X |
| 4,499,052 | 2/1985 | Fulwyler | 436/63 X |
| 4,569,946 | 2/1986 | LeVeen | 514/693 |
| 4,717,655 | 1/1988 | Fulwyler | 435/34 X |
| 4,751,179 | 6/1988 | Ledis et al. | 435/34 |

OTHER PUBLICATIONS

Hawley, The Condensed Chemical Dictionary, New York, Van Nostrand Reinhold, Tenth edition, 1981, p. 959.
Hoffman et al. Proceedings National Academy Science USA, vol. 77, No. 8, Aug. 1980, pp. 4914-4917.
Salzman et al., Acta Cytologica, vol. 19, No. 4, 1975, pp. 374-377.
The Merck Index, tenth edition (Windholz editor), Merck & Co., Rahway, N.J., (1983), p. 647.
D. Y. Mason et al. Annals N.Y. Academy of Science vol. 420, pp. 127-138 (1983).
R. A. Thomas et al. J. Histochemistry and Cytochemistry, vol. 25, No. 7, pp. 827-835 (1977).
James R. Downing et al, Laboratory Management, May 1984, pp. 29-37.
R. C. Leif et al, Clinical Chemistry 23, 1492-1498 (1977).

*Primary Examiner*—Robert J. Hill, Jr.
*Attorney, Agent, or Firm*—Meredith P. Sparks; Gerald R. Hibnick

[57] ABSTRACT

Specified classes and subclasses of leukocyte blood cells are identified by immunohematology procedures, based on utilization of antigenic determinants on the cell surface, their reactivity with antibodies which fluoresce under known circumstances, and identified by utilization of principles of flow cytometry or morphology.

This invention particularly concerns improvements in the lysing and fixing method used prior to detection and identifying of the cells. In this method, a whole blood sample first is incubated with a reagent including antibodies to the cell subclass to be identified, the antibodies having directly or indirectly made fluorescently responsive to a particular light (e.g. argon ion laser). The red blood cells then are lysed with a reagent containing saponin. Next follows a leukocyte fixing treatment, preferably using a cross-linking dialdehyde composition, such as glyoxal or glutaraldehyde.

Details are given as to time, temperature, concentration, and the use of additives and stains, as well as the use of particular monoclonal antibodies in the preferred procedure.

26 Claims, 1 Drawing Sheet

REAGENT SYSTEM AND METHOD FOR IDENTIFICATION, ENUMERATION AND EXAMINATION OF CLASSES AND SUBCLASSES OF BLOOD LEUKOCYTES

This application is a continuation of application Ser. No. 866,985, filed May 15, 1986, now abandoned, which is a continuation of application Ser. No. 615,961, filed May 31, 1984, now abandoned.

BACKGROUND OF THE INVENTION

This invention relates to immunohematology procedures, and more particularly to a reagent system and a method for the identification of classes as well as subclasses within a class and enumeration of cells within those subclasses of blood leukocytes from a whole blood sample which has been incubated with a fluorescent responsive antibody to a select antigenic determinant on the surface of specified subclasses of blood leukocytes.

It is known that the lymphocyte population of blood leukocytes is subdivided into a number of subclasses which play distinct roles in the immune response. In disease states the relative number of lymphocytes found in various subclasses is likely to change. Hence, the enumeration and identification of the cells in the various subclasses will provide useful information in the study and treatment of disease as described by James R. Downing et al in Laboratory Management, May 1984, pages 29-37.

It is known that several particular subclasses of functionally distinct lymphocytes and other blood leukocytes can be identified on the basis of antigenic determinants on the cell.

Monoclonal antibody techniques have been utilized to produce large quantities of highly purified antibody to various lymphocyte and other leukocyte subclasses. Utilizing such antibodies, it has proved feasible to assay the lymphocytes of an individual to determine the relative number of cells in various subclasses. Further, utilizing direct or indirect techniques, the antibodies can be labeled fluorescently, thereby rendering the samples under consideration amenable to flow cytometric analysis and morphology. More recently, additional monoclonal antibodies have been developed which include several that react with monocytes and granulocytes.

Hansen et al described in U.S. Pat. No. 4,284,412, 1981, and in Immunology, Vol. 77, No. 8, pp 4914-4917 (1980) a method and apparatus for automated identification an enumeration of specified lymphocyte subclasses. An anticoagulated whole blood sample or buffy coat sample is incubated with an antibody to a specific lymphocyte subclass of interest. The binding of this antibody is detectable if either it has been coupled with a fluorescent chemical moiety (the direct technique), or if it in turn is specifically bound by another macromolecule to which has been coupled a fluorescent dye moiety (the indirect technique). These fluorescent moieties possess the characteristic of emitting fluorescent light upon illumination with incident laser light. The sample then is lysed using ammonium chloride as the lysing agent. A diluted sample then is subjected to flow cytofluorometric analysis. Four clusters of cells are distinguished. However, only three clusters are found to be due to leukocytes. These clusters were identified as (1) lymphocytes, (2) monocytes and (3) granulocytes. The fourth cluster is identified as aggregates or multiples of platelets and red blood cell debris due to incomplete lysing of the red blood cells.

The lysing techniques described in these references now have been improved by the present invention so as to maintain better the morphology of the immunologically labeled specific leukocytes, improve their stability on storage, and render them more suitable for cytofluorescent analysis, or for other operations such as microscopic examination of stained cells on a slide.

Employed herein are the trademarks COULTER, COULTER CLONE, ISOTON, E.A.SY.1, MDADS and EPICS which are owned by Coulter Corporation or Coulter Electronics, Inc.

BRIEF DESCRIPTION OF THE DRAWINGS

FIG. 1A shows a sample with T4-FITC, as in Example 1.

FIG. 1B shows a control with no fluorescent antibody added.

SUMMARY OF THE INVENTION

Figure 1A:
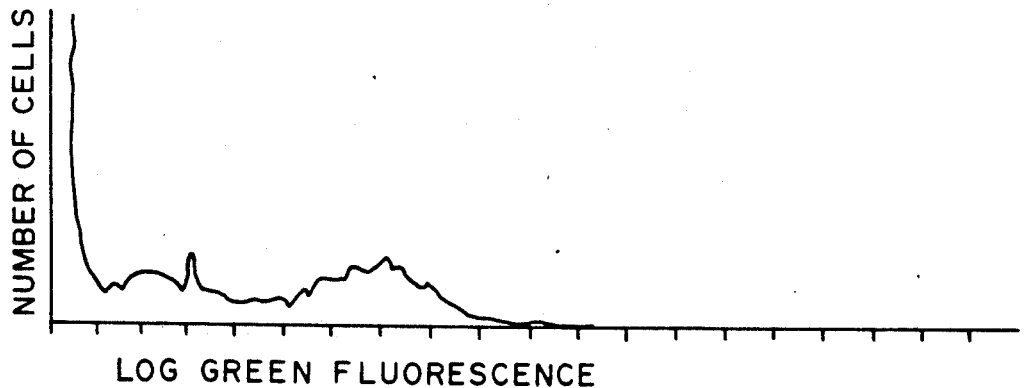
FIGS. 1A and 1B show the cell-membrane-antigen histograms produced by flow cytometric analysis. The abscissa represents a value directly proportional to the log of the green fluorescence intensity. The ordinate represents the number of cells counted in each channel on a relative scale.
Figure 1B:
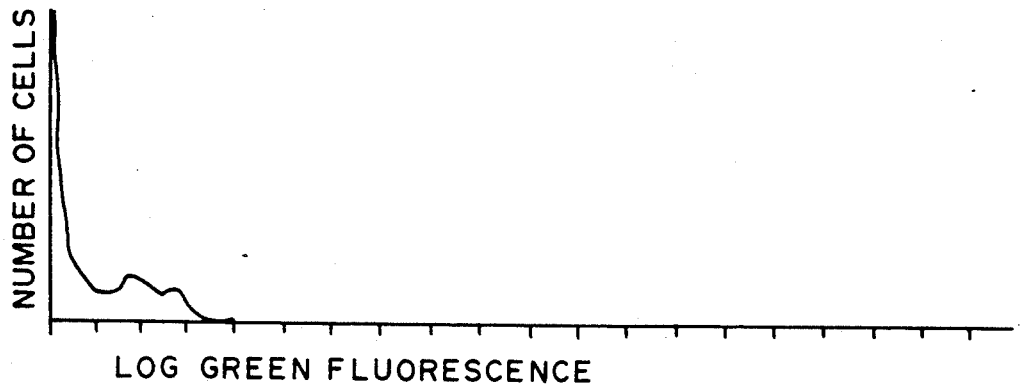
Figure 2:
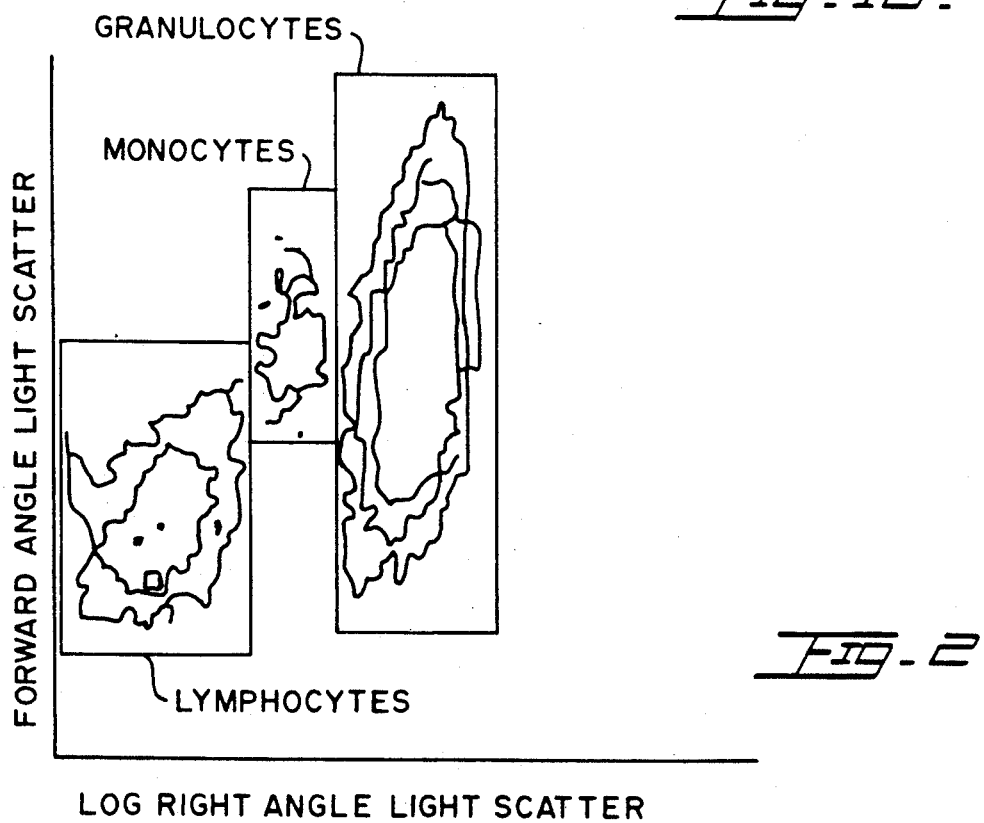
FIG. 2 is a contour map in which the abscissa represents the log of the right angle light scatter intensity, and the ordinate represents the forward angle light scatter intensity. The rectangles designate the specific areas of this two dimentional distribution which contain the specific leukocyte cell classes: lymphocytes, monocytes, granulocytes. This contour map is determined from the two dimensional data by a flow cytometer. Each contour line designates the locations on the map where there is essentially the same number of cells, irrespective of light scatter intensity.

This invention relates to an improved reagent system and method for identifying classes and enumerating the cells in selected subclasses within those classes of leukocytes in whole blood, based on utilization of antigenic determinants on the cell surface and their reactivity with labeled antibodies. This invention employs somewhat the general overall procedure described by Hansen et al, but with improvements especially over the conventional lysing and cell fixing procedure.

According to the present invention, the reagent system comprises aqueous solutions of (A) a lysing reagent containing saponin, and (B) a fixing reagent containing a cross-linking agent. The improved reagent system lyses the blood erythrocytes, while maintaining the physical and morphological properties of the blood leukocyte classes, as well as labeling specific leukocyte subclasses. The samples can be analyzed either by the principles of flow cytometry, or by microscopic morphology.

Using saponin as the lysing agent, the method permits fixation with a limited amount of a cross-linking fixative. This is accomplished by lysing at room temperature, or preferably at an elevated temperature, such as 42° C., which selectively destabilizes the erythrocyte membrane and accelerates the lysing reaction. The use of a hypotonic buffer, consisting primarily of potassium salts, also favors lysis.

Glyoxal is preferred over glutaraldehyde as the cross-linking agent, even though the latter is a stronger fixative; because glyoxal, after reacting with a leukocyte, imparts minimal, if any, background fluorescence; whereas glutaraldehyde produces a significant amount of fluorescence. Dialdehydes are preferred over monoaldehydes, such as formaldehyde, which have only a weak cross-linking action for this purpose.

The addition of dimethyl sulfoxide or urea to the fixative improves the reaction, and tends to decrease the amount of fixative required to retard the action of the saponin on the leukocytes. In addition, a temperature drop to approximately 4° C. (as by use of an ice bath) slows down the reaction. The cells are weakly fixed and can be sufficiently spread on a slide for cytological preparation.

In copending U.S. application Ser. No. 615,966, now U.S. Pat. No. 4,751,179 filed May 31, 1984 the same day as the present application, a somewhat analogous lysing method is described, but such method does not include immunological techniques for utilizing antigenic determinants on the cell surface and their reactivity with antibodies that label cells which fluoresce under known circumstances.

DETAILED DESCRIPTION OF THE INVENTION

This invention concerns a method for identifying classes and enumerating cells in subclasses of leukocytes in whole blood, based on the utilization of antigenic determinants on the cell surface and their reactivity with labeled antibodies, followed by utilization of the principles of flow cytometry or microscopic morphology to identify the cells which have been labeled.

Employed herein are the terms "lysis", or forms thereof, and "morphology". Lysis of the erythrocytes means to render the erythrocytes such that they no longer are detectable by physical techniques, or the erythrocyte residue is such that the signals they generate are sufficiently decreased that they will not interfere with those produced by the blood leukocytes. Morphology means the process of microscopic examination of cells and the determination of their classes and subclasses by either human or artificial intelligence techniques.

According to this invention, a whole blood sample is incubated with diluted monoclonal antibody to label certain subclasses of leukocytes. The erythrocytes then are removed by lysis, and the leukocytes are stabilized by use of a cross-linking fixative, prior to the class and subclass identification. It is preferable to lyse the red blood cells before the steps of identifying the class and subclasses of leukocytes, to avoid the danger that coincident passage of two or more erythrocytes or fragments thereof through counting transducer could be mistaken for white blood cells. A preferred procedure is to lyse the red blood cells prior to the identification of the leukocytes by addition of a lysing reagent to the suspension of cells so as to cause the red blood cells to rupture and release their hemoglobin content into the solution.

The problem is to lyse the red blood cells without damage to the antigen-antibody complexes on the leukocytes, while preserving their cell morphology and producing a stable cellular suspension.

The whole blood sample must be treated in a way that lyses the red blood cells, and at the same time the leukocyte blood cells are maintained in a condition which allows measurements to differentiate them and their subclasses. The lysing reagent needs to act quickly, preferably in less than one minute. The cytogram produced should have the cluster of aggregates or multiplets of platelets, and red cell debris separate from the leukocyte clusters.

In a preferred embodiment of the invention, the whole blood sample is incubated with a fluorochromed antibody to label a specific subclass of leukocytes. The erythrocytes are selectively lysed with a lysing reagent containing saponin, and the directly labeled leukocytes are then fixed, using a fixing reagent containing a dialdehyde. The leukocyte cell suspension then is analyzed by the combination of forward angle and right angle light scattering to yield data representing at least three classes. The positively immunofluorescent leukocyte populations are enumerated with a COULTER ® EPICS ® flow cytometer. The fixative is a cross-linking or bifunctional fixative, preferably a dialdehyde.

Successful results have been obtained with the following COULTER CLONE ® antibodies: T4-FITC, T8-FITC, T11, T11-FITC, B1-FITC and Mo2-FITC. Other antibodies useful for this purpose would include OKT1.PAN, OKT4.IND, and also OKM1.M/G, which reacts with monocytes and granulocytes.

As used herein "fluorescent responsive antibody" refers to antibodies which themselves fluoresce, or antibodies which are labeled to fluoresce under specified stimulation.

A technique has been developed to lyse the blood erythrocytes, while maintaining the physical properties and morphology of the blood leukocytes, and immunologically labeling specific leukocyte subclasses. This technique is unique in that it does not involve centrifugation; yet, it does preserve the cells sufficiently so that they can be stored at 4° C. for a day and still be usable for flow analysis. Using this technique, it is possible, for example, to divide T lymphocytes into (1) helper lymphocytes, using COULTER CLONE T4-FITC monoclonal antibody, and (2) suppressor lymphocytes, using COULTER CLONE T8-FITC monoclonal antibody.

The cells prepared by the techniques of this invention also are suitable for other cytological preparations, for instance by centrifugal cytology.

The technique of this invention minimizes the concentration of the saponin lysing reagent required, and consequently permits fixation with a limited amount of fixative. Lysing is accomplished at room temperature, or preferably at an elevated temperature such as 42° C., which selectively destabilizes the erythrocyte membrane and accelerates the lysing reaction. The use of a hypotonic buffer, consisting primarily of potassium salts, also favors lysis.

It has been found that the amount of saponin employed under comparable conditions of lysis can be decreased as the temperature is increased. Thus, the residual amount of saponin in preparations that are not centrifuged can be minimized by increasing the temperature of the lysing reagent.

Bifunctional or cross-linking fixing agents such as glyoxal, glutaraldehyde, carbodiimide, succinaldehyde, Mirsky's reagent, and the like, are suitable for use in the fixing reagent. Mirsky's reagent consists primarily of an impure preparation of glyoxal derived from the chemical treatment of saccharides. Glyoxal is especially preferred in the fixing reagent, because it does not fluoresce. This is an advantage when determining the fluorescence of the antibody binding cells later on in the procedure.

The invention is not limited to fluorescence measurements, but absorbance measurement can be performed such as is described in "Defined Immunofluorescence and Related Cytochemical Methods" by D. Y. Mason, Z. Abdulaziz and B. Falini, Annuals of the New York Academy of Science, Vol. 420, pages 127–138 (1983).

The technique of this invention can be employed with the additional physical measurements of DC and AC impedance. The measurements can be utilized in conjunction with the aforementioned light scattering measurements, or in place of them.

The fixed blood cells are stable when stored cold at about 2° to 4° C. prior to the light scattering procedure. A laboratory study established that samples were stable for 24 hours post lyse. For example, using COULTER CLONE antibody T8-FITC, the percent positive cells was $20.3 \pm 1.0$ immediately after sample preparation, $20.3 \pm 0.6$ after 20 hours post lyse, and $20.0 \pm 0.3$ at 24 hours post lyse.

Centrifugation and removal of the supernatant fluid between processing steps is beneficial in that it significantly decreases cell debris, and removes excess loosely bound antibody. However, centrifugation has the disadvantage that it virtually precludes obtaining an absolute count of the cells present, and under some conditions can result in selective cell loss. Although centrifugation can be part of a semiautomated system, it introduces considerable complexity into a completely automated system.

One of the major constraints in the development of the present reagent system is that sample preparation for a flow cytometer, such as an EPICS system, unlike that for a standard hematology analyzer, such as the COULTER ® Model S series instrument, is asynchronous. The time between the final sample preparation and measurement can range from almost immediately to the next day.

One other problem is the choice of a suitable control. The exquisite specificity of monoclonal antibodies in some cases for example, when fluoresceinated mouse immunoglobulin G (mouse IgG-FITC) is used as a control, leads to an over-estimation of background fluorescence. Either a preincubation and/or a simultaneous incubation with unlabeled antibody blocks the nonspecific binding sites, and this in many cases can eliminate the need for a control.

Samples containing antibody prepared according to this invention are capable of being prepared employing Romanowsky stain. It is also possible in the case of fluorescent studies to stain the cell with two stains, such as dichlorofluorescin and 4,6-diamino-2-phenylindole (DAPI). Other conventional stains include Mithromycin and Acridine Orange.

The examples which follow illustrate certain of the methods and procedures followed in the invention.

EXAMPLE 1

Cell Preparation: The lyse and fixative reagents are prepared at room temperature, approximately 24° C.

1. The 100 ul of phosphate buffered saline (PBS) is added into a $16 \times 100$ tube followed by 100 ul of whole blood. The tube contents then are gently mixed by swirling.

2. The 5 micrograms of COULTER CLONE monoclonal T11 antibody is added into the same tube and mixed gently. The tube then is kept at room temperature approximately 24° C., for 20 minutes, with occasional shaking.

3. The sample, since this was an indirect fluorescence technique, was washed twice by centrifugation with 4 ml PBS. The sample then was treated with 85 micrograms of fluoresceinated goat antimouse antibody and incubated for 20 minutes, and washed as before with 4 ml of PBS.

4. The cells were suspended in 1 ml of a solution consisting of 3 g NaCl and 1 g NaHCO$_3$ and water to one liter.

5. The 100 ul of lyse reagent consisting of: 24 g saponin, 4.0 g NaCl, 1 g sorbic acid and water to one liter then is added to the tube containing blood, including the indirectly labeled T lymphocytes and continuously agitated for eight seconds.

6. At the end of the 8 second lysis, 1000 ul of the fixative reagent is added to the lysed sample. This fixative reagent consisted of: 6.0 g of NaCl, 22 g of glutaraldehyde, brought up to one liter volume with water.

7. The sample which is indirectly labeled with monoclonal antibody, lysed and then fixed must be analyzed with the flow cytometer within 15 minutes, because of the development of glutaraldehyde induced autofluorescence. Filtration of the sample, preferable through a 37 micron mesh, is desirable.

Sample Analysis: The samples are analyzed with the COULTER EPICS V single laser, flow cytometer system. The system configuration is set up as herein explained. The laser emits 500 mw of 488 nm radiation. The preferred filter configuration is a 515 interference acting as a blocking filter for green fluorescence, 488 nm dichroic mirror and an ND1 filter for orthogonal light scatter,a nd a ND1 filter for forward angle light scatter. The data are analyzed with a computer system, such as in the COULTER MDADS ® or E.A.SY.1 ®. The three parameters measured are log fluorescence, low angle light scatter and log right angle light scatter. This analysis procedure also is utilized for each of the following Examples.

EXAMPLE 2

Cell Preparation: The lyse and fixative reagents are prepared at 37° C. The reagents can be kept capped in a water bath throughout the procedure.

1. A 100 ul portion of labeling diluent, consisting of 1.0 g of NaN$_3$, 1.36 g KH$_2$PO$_4$, 1.31 g of K$_2$HPO$_4$ and 3.73 g of KCl, brought up ton one liter volume with water, is added into a $16 \times 100$ tube, followed by 100 ul of whole blood. The tube contents are then gently mixed by swirling.

2. Ten micrograms of a non-specific, unlabeled mouse antibody is added to block any non-specific binding of the monoclonal antibody.

3. One microgram of COULTER CLONE monoclonal antibody T4-FITC is added into the same tube and mixed gently. The tube is then placed in a water bath maintained at 37° C. for five minutes, with occasional shaking.

4. The 100 ul of a lyse reagent consisting of 4 saponin, 1.75 g of NaCl, 1.36 g of KH$_2$PO$_4$, 1.31 g of K$_2$HPO$_4$ and 2.24 g of KCl, brought up to one liter volume with water, is then added to the tube containing blood and antibody, and continuously is agitated in the water bath for one minute.

5. At the end of the one minute lysis, 500 ul of a fixative reagent is added to the lysed sample, mixed gently, and kept in the water bath at 37° C. for an additional five minutes, mixing occasionally. This fixative reagent consists of 11.7 g of NaCl, 0.43 g of calcium gluconate, 21 of glyoxal, 220 g of dimethyl sulfoxide and 25 g of Carbowax 1450 brought up to one liter volume with water.

At this point in time the whole blood has been labeled with monoclonal antibody, lysed and then fixed. It is now ready for analysis with the EPICS flow cytometer. Filtration of the sample, preferably through a 37 micron mesh, is desirable. The samples are stabilized at approximately 2° C. on ice, if need-be, for at least 5 minutes prior to sample analysis. Analysis is as stated at the end of Example 1.

In accordance with the above procedure, but substituting for the COULTER CLONE monoclonal T4-FITC of Example 1, any one of the following COULTER CLONE monoclonal antibodies: T8-FITC; T11-FITC; B1-FITC; Mo2-FITC; similar results are obtained. In each instance the leukocyte subclass which is labeled is the leukocyte which is specific from the antibody employed.

EXAMPLE 3

Cell Preparation: The lyse and fixative reagents are prepared at 24° C. The reagents can be kept capped in a water bath throughout the procedure.

1. The 100 ul of a labeling diluent consisting of 1.0 g of $NaN_3$, in 1 liter ISOTON® Plus diluent is added into a 16×100 tube followed by 100 ul of whole blood. The tube contents are then gently mixed by swirling.

2. COULTER CLONE monoclonal antibody T4-FITC is added in the amount of one microgram into the same tube, mixed gently, and then placed in a test tube rack at room temperature (24° C.) for five minutes, shaking occasionally.

3. The 1000 ul of lyse reagent, consisting of 0.5 g of saponin, 3.72 g of KCl, 1.36 g of $KH_2PO_4$, and 1.31 g of $K_2HPO_4$, brought up to one liter volume with water, is then added to the tube containing blood and antibody, vortexed gently for 30 seconds and placed in a rack at room temperature (24° C.) for five minutes, mixing gently each minute.

4. At the end of the five minute lysis, 1000 ul of the fixative reagent consisting of 12.6 g of NaCl, 220 g of dimethyl sulfoxide, 200 ml of Mirsky's reagent and 600 ml of ISOTON Plus diluent, is added to the lysed sample, mixed gently, and kept at room temperature (approximately 24° C. ) for an additional five minutes, mixing occasionally. Mirsky's reagent is commercially available from Mirsky's National Diagnostics, Somerville, N.J.

At this point in time the whole blood has been labeled with monoclonal antibody, lysed and then fixed. It is ready for analysis with the EPICS flow cytometer. Filtration of the sample, preferably through a 37 micron mesh, is desirable.

The samples are stabilized on ice, if need be, for at least 5 minutes prior to sample analysis, and analyzed as stated at the end of Example 1.

EXAMPLE 4

Cell Preparation: The lyse and fixative reagents are prepared at 42° C. The reagents can be kept capped in a water bath throughout the procedure.

1. The 100 ul of a labeling diluent, consisting of 1.0 g of $NaN_3$ in 1 liter of ISOTON Plus diluent, is added into a 16×100 tube followed by 100 ul of whole blood. The tube contents are then gently mixed by swirling.

2. Four micrograms of COULTER CLONE monoclonal antibody T4-FITC are added into the same tube, mixed gently, and then placed in the water bath maintained at 42° C. for five minutes, shaking occasionally.

3. The lyse reagent, consisting of 24 g of saponin, 4.0 g of NaCl, 1.0 g sorbic acid and water to make 1 liter is prepared. Ten milliliters of this lyse reagent is then diluted with 1 liter of lyse diluent consisting of 1.31 g $K_2HPO_4$ and 1.36 g $KH_2PO_4$ in distilled water. 1000 ul of the mixture is added to the tube containing blood and antibody, and the tube is continuously agitated in the water bath for one minute.

4. At the end of a 30 second lysis, 1000 ul of the fixative reagent consisting of 12.6 g of NaCl, 200 ml of Mirsky's reagent, 220 g of dimethyl sulfoxide, and 600 ml of ISOTON Plus diluent brought up to 1 liter volume with water, is added to the lysed sample, mixed gently, and kept in the water bath at 42° C. for an additional five minutes, mixing occasionally.

At this point in time the whole blood has been labeled with monoclonal antibody, lysed and then fixed. It is ready for analysis with the EPICS flow cytometer. Filtration of the sample, preferably through a 37 micron mesh, is desirable.

The samples are stabilized on ice, if need be, for at least 5 minutes prior to sample analysis and analyzed as stated at the end of Example 1.

EXAMPLE 5

Cell Preparation: The lyse and fixative reagents are prepared at 37° C. The reagents can be kept capped in a water bath throughout the procedure.

1. A 100 ul portion of labeling diluent, consisting of 1.0 g of $NaN_3$, 1.36 g $KH_2PO_4$, 1.31 g of $K_2HPO_4$ and 3.73 g of KCl, brought up to one liter volume with water, is added into a 16×100 tube, followed by 100 ul of whole blood. The tube contents are then gently mixed by swirling.

2. Ten micrograms of a non-specific, unlabeled mouse antibody is added to block any non-specific binding of the monoclonal antibody.

3. One microgram of COULTER CLONE monoclonal antibody T8-FITC is added into the same tube and mixed gently. The tube is then placed in a water bath maintained at 37° C. for five minutes, with occasional shaking.

4. The 100 ul of a lyse reagent consisting of 4 g saponin, 1.75 g of NaCl, 1.36 g of $KH_2PO_4$, 1.31 g of $K_2HPO_4$ and 2.24 g of KCl, brought up to one liter volume with water, is then added to the tube containing blood and antibody, and continuously is agitated in the water bath for one minute.

5. At the end of the one minute lysis, 500 ul of a fixative reagent is added to the lysed sample, mixed gently, and kept in the water bath at 37° C. for an additional five minutes, mixing occasionally. This fixative reagent consists of 11.7 g of NaCl, 0.43 g of calcium gluconate, 21 g of glyoxal, 220 g of dimethyl sulfoxide and 25 g of Carbowax 1450 brought up to one liter volume with water.

At this point in time the whole blood has been labeled with monoclonal antibody, lysed and then fixed. It now is ready for analysis with the EPICS flow cytometer equipped with the COULTER CVA, employing the principles proposed for the AMAC III, R. C. Leif et al, Clinical Chemistry 23, 1492-8 (1977); and R. A. Thomas et al, J. Histochemistry and Cytochemistry, Vol. 25, No. 77, pp 827-835 (1977). The designator COULTER "CVA" represents "cell volume accessory" and, in quite simple terms, means that the electronic cell analysis equipment utilizing the well known Coulter principle of particle detection has been utilized and integrated into a flow cytometer. Such multiparameter instrument has been demonstrated commercially. Filtration of the sample, preferably through a 37 micron mesh, is essential. The samples are stabilized on ice, if need be, for at least 5 minutes prior to sample analysis. The parameters measured were forward angle light scattering, right angle light scattering, fluorescein immunofluorescence and electronic cell volume.

EXAMPLE 6

Cell Preparation: The lyse and fixative reagents are prepared at 42° C. The reagents are kept capped in a water bath throughout the procedure.

1. One hundred ul of labeling diluent consisting of 1 g of $NaN_3$, in 1 liter of ISOTON Plus diluent is added into a 16×100 tube followed by 100 ul of whole blood. The contents are then gently mixed by swirling.

2. Four micrograms of COULTER CLONE monoclonal antibody T4-FITC are added into the same tube. The tube is mixed gently, and then placed in the water bath maintained at 42° C. for five minutes, shaking occasionally.

3. Then 100 ul of lyse reagent, consisting of 0.4 g saponin, 0.05 g of sorbic acid, 1.36 g of $KH_2PO_4$, 1.31 g of $K_2HPO_4$, 3.72 g of KCl, and water to make one liter, is added to the tube containing blood and antibody and continuously agitated in the water bath for 30 seconds.

4. At the end of the 30 second lysis, 1000 ul of a fixative reagent consisting of 12.6 g of NaCl, 220 g of dimethyl sulfoxide, 200 ml of Mirsky's reagent, and 600 ml of ISOTON Plus diluent, is added to the lysed sample, mixed gently, and kept in the water bath at 42° C. for an additional five minutes, mixing occasionally.

At this point in time the whole blood has been labeled with monoclonal antibody, lysed and then fixed. It is ready for analysis with the EPICS flow cytometer. Filtration of the sample, preferably through a 37 micron mesh, is desirable. The samples are stabilized on ice, if need be, for at least five minutes prior to sample analysis and analyzed as stated in Example 1.

EXAMPLE 7

Cell Preparation: The lyse and fixative reagents are prepared at 37° C. The reagents can be kept capped in a water bath throughout the procedure.

1. The 100 ul of a labeling diluent, consisting of 1.0 g of $NaN_3$, 1.36 g of $KH_2PO_4$, 1.31 g of $K_2HPO_4$ and 3.73 g of KCl, brought up to 1 liter volume with water, is added into a 16×100 tube followed by 100 ul of whole blood. The tube contents are then gently mixed by swirling. To this is then added 10 ul of a staining solution consisting of 0.025 g of 4,6-diamino-2-phenylindole (DAPI) in 10 ml of absolute ethanol.

2. Ten micrograms of a non-specific unlabeled mouse antibody is added to block any non-specific binding of the monoclonal antibody. The tube is mixed gently and then placed in the water bath maintained at 37° C. for five minutes, shaking occasionally.

3. One microgram of COULTER CLONE monoclonal antibody T8-FITC is added into the same tube. The tube is mixed gently, and then placed in the water bath maintained at 37° C. for five minutes, shaking occasionally.

4. To the tube containing the staining solution, blood and antibody, is added 100 ul of lyse reagent. This reagent consists of 4 g of saponin, 1.75 g of NaCl, 1.36 g of $KH_2PO_4$, 1.31 g of $K_2HPO_4$, 2.24 g of KCl, and water to make one liter volume. After the reagent is added, the tube is continuously agitated in the water bath for one minute.

5. At the end of the one minute lysis, 500 ul of a fixative reagent consisting of 11.7 g of NaCl, 0.43 g of calcium gluconate, 21 g of glyoxal, 220 g of dimethyl sulfoxide, 25 g of Carbowax 1450, and water to make one liter, is added to the lysed sample, mixed gently, and kept in the water bath at 37° C. for an additional five minutes, mixing occasionally.

At this point in time the whole blood has been labeled with the monoclonal antibody T8-FITC and DAPI, lysed and then fixed. It is ready for preparation by centrifugal cytology. The samples are stabilized on ice, if need be, for at least 5 minutes prior to sample analysis.

6. A standard microscope slide is prepared with a poly-d-lysine solution consisting of 50 mg of poly-d-lysine having a molecular weight of approximately 700,000, by dipping the slide in the solution, and then drying on a slide dryer maintained at 60° C.

7. A pair of Leif Centrifugal Cytology buckets (U.S. Pat. No. 4,250,830) is assembled and the lysed blood sample is spun for five minutes at 1,500 rpm. The supernatant fluid is removed, and the sample is washed three times with the labeling diluent.

8. The supernatant fluid is removed and the cells in the labeling diluent on the slide are coverslipped. The slide is now ready for microscopic examination with a mercury arc ultraviolet excitation for DAPI, and visable excitation for FITC.

As can be seen from the preceding examples, the relative volumes of the blood sample 50 to 100 ul, the lysing reagent 100 to 1000 ul, and the fixative 500 to 1000 ul can vary. The lysing reagent 0.24 to 4 g/L and fixative concentrations 0.66 g/L to 40 g/L are inversely related to their volumes and must be scaled up as the volume of all previously added reagents is increased. The quantity of saponin 0.24 to 4.0 g/L also is inversely related to both the temperature 24° C. to 60° C. and the period for lysis 38 seconds to 5 minutes. The quantity of fixative also is related to whether the sample is to be stored for a prolonged period or used immediately for morphology. For the long term storage, maximum fixation is essential, but for the near immediate use, minimal fixation often is preferable.

It is understood that the illustrative embodiments set forth herein constitute examples of the principles of the present invention, but that numerous alternatives will occur to those of ordinary skill in the art, without departure from the scope of this invention.

We claim:

1. In a process for identifying classes, or classes and also selected subclasses of leukocytes in whole blood, such identifying being based on utilization of antigenic determinants on leukocyte cell surfaces and their reactivity with labeled antibodies, which process includes the steps of:
    (a) incubating a sample containing whole blood with an antibody as so to label a specific leukocyte class and/or subclass of interest;
    (b) lysing erythrocytes in the sample; and then
    (c) subjecting the incubated sample to flow cytometric analysis; the improvement comprising:
        A. conducting said incubating step prior to said lysing step;
        B. lysing the erythrocytes in the incubated sample with an aqueous solution of a lysing reagent containing saponin for a predetermined time and temperature conditions;

C. then treating leukocytes in the incubated sample with a fixing reagent containing a cross-linking compound for a predetermined time and temperature conditions, said fixing reagent containing a non-fluorescing dialdehyde as an active ingredient;

D. the physical properties, or the physical properties and also the morphological properties of the leukocytes being maintained in condition for the cytometric analysis; and E. said analysis including at least optical detection to identify the specific leukocyte class and/or subclass of interest.

2. The process of claim 1 wherein specific leukocyte subclasses are labeled and the cells in those subclasses are enumerated.

3. The process of claim 1 wherein in step (c) a combination of at least two types of physical measurements is employed for identifying leukocyte classes and/or subclasses, and wherein the distribution of each leukocyte class and/or subclass is measured by its fluorescent intensity.

4. The process of claim 3 wherein at least one of said physical measurements is electronic impedance.

5. The process of claim 3 wherein said physical measurements are a combination of electronic impedance and right angle light scattering.

6. The process of claim 3 wherein leukocytes in the incubated sample are classified by morphology, and subclassified by fluorescent intensity.

7. The process of claim 1 wherein said lysing reagent contains saponin in a concentration of about 0.24 g per liter to about 4 g per liter.

8. The process of claim 1 wherein said temperature for lysing is from about 24° C. to about 42° C.

9. The process of claim 1 wherein said time of lysing is 8 seconds to about 5 minutes.

10. The process of claim 1 wherein fixing reagent contains glutaraldehyde.

11. The process of claim 1 wherein said non-fluorescing dialdehyde is glyoxal.

12. The process of claim 11 wherein said glyoxal is present in a concentration of 0.66 g to 40 g per liter in the fixing reagent; or 0.33 g to 20 g per liter in the incubated and lysed sample with the fixing reagent added.

13. The process of claim 1, further comprising: accomplishing said steps of incubating, lysing and subjecting in the absence of centrifugation.

14. A reagent for use on a whole blood sample for identifying classes, or classes and also subclasses of leukocytes at least one of which has been labeled with specific antibodies, said reagent comprising: a lysing reagent containing an amount of saponin sufficient, within a predetermined time and at a suitable temperature, for lysing erythrocytes in a manner which leaves labeled leukocytes substantially intact; and a fixing reagent containing a cross-linking agent in such amount sufficient, within a predetermined time and at a suitable temperature, for maintaining the physical properties, or the physical properties and also the morphological properties of leukocytes for leukocyte identifying by at least optical detection; said fixing reagent containing a non-fluorescing dialdehyde as an active ingredient.

15. The reagent of claim 14 wherein said lysing reagent contains saponin in a concentration of about 0.24 g per liter to about 4 g per liter.

16. The reagent of claim 14 wherein said fixing reagent contains glutaraldehyde.

17. The reagent of claim 14 wherein said non-fluorescing dialdehyde is glyoxal.

18. The reagent of claim 17 wherein said glyoxal is present in a concentration of 0.66 g to 40 g per liter.

19. The reagent of claim 14 wherein said lysing reagent contains sorbic acid as an additive.

20. The reagent of claim 14 in which said fixing reagent also contains dimethyl sulfoxide.

21. The reagent of claim 14 in which said fixing reagent also contains urea.

22. The reagent of claim 14 which further includes at least one dye to stain leukocytes.

23. The reagent of claim 14 which further includes antibodies linked to a fluorochrome for labeling of some leukocytes.

24. In a process for identifying classes, or classes and also selected subclasses of leukocytes, such identifying being based on utilization of antigenic determinants on leukocyte cell surfaces and their reactivity with labeled antibodies, which process includes the step of:

(a) incubating a sample containing whole blood with an antibody as so to label a specific leukocyte class and/or subclass of interest; wherein the improvement comprises; the steps of treating leukocytes with a fixing reagent containing a cross-linking compound of which a non-fluorescing dialdehyde, glyoxal, is an active ingredient; and then identifying the treated leukocytes by at least optical detection.

25. The process of claim 24 wherein said glyoxal is present in a concentration of 0.66 g to 40 g per liter in the fixing reagent; or 0.33 g to 20 g per liter in the leukocytes with the fixing reagent added.

26. In a process for identifying classes, or classes and also selected subclasses of leukocytes, such identifying being based on utilization of antigenic determinants on leukocyte cell surfaces and their reactivity with labeled antibodies, which process includes the step of:

(a) incubating a sample containing whole blood with an antibody as so to label a specific leukocyte class and/or subclass of interest; wherein the improvement comprises; the steps of treating leukocytes, in the absence of centrifuging, with a fixing reagent containing a cross-linking compound of which a non-fluorescing dialdehyde is an active ingredient; and then identifying the treated leukocytes by at least optical detection.

* * * * *